United States Patent [19]

Seemann et al.

[11] Patent Number: 5,645,817
[45] Date of Patent: Jul. 8, 1997

[54] GRANULOCYTE-BINDING ANTIBODY CONSTRUCTS, THEIR PREPARATION AND USE

[75] Inventors: Gerhard Seemann, Marburg-Elnhausen; Klaus Bosslet, Marburg, both of Germany

[73] Assignee: Behringwerke Aktiengesellschaft, Marburg, Germany

[21] Appl. No.: 459,310

[22] Filed: Jun. 2, 1995

Related U.S. Application Data

[63] Continuation of Ser. No. 100,963, Aug. 3, 1993, abandoned.

[30] Foreign Application Priority Data

Aug. 5, 1992 [DE] Germany ............... 42 25 853.7

[51] Int. Cl.$^6$ ............... C12P 21/08; A61K 39/395; A61K 39/44; C07K 16/28
[52] U.S. Cl. ............... 424/9.341; 424/133.1; 424/134.1; 424/135.1; 424/153.1; 514/12; 530/350; 530/387.3; 530/388.7; 530/391.1
[58] Field of Search ............... 530/350, 387.3, 530/388.7, 388.85, 391.1; 514/12; 424/134.1, 135.1, 153.1

[56] References Cited

FOREIGN PATENT DOCUMENTS

| | | |
|---|---|---|
| 0 097 630 A2 | 1/1984 | European Pat. Off. |
| 0 328 404 A1 | 8/1989 | European Pat. Off. |
| 0 353 018 A1 | 1/1990 | European Pat. Off. |
| WO91/09968 | 7/1991 | WIPO |
| WO92/01059 | 1/1992 | WIPO |

OTHER PUBLICATIONS

Burgess et al. Journal of Cell Biology 111: 2129–2138 1990.
Gillies et al (1990) Human Antibod. and Hybridomas 1(1) p. 47.
Lazar et al. Molecular and Cellular Biology 1988 p. 1247.
Tao et al. Journal of Immunology vol. 143 2595 1989.
Harris et al. TibTech. vol. 11 (1993.) p. 42.
Bird et al. Trends in BioTech. 9, pp. 132–137 (1991).
D'Amico et al. Nuc. Med Biol. 18(1) 145 (1991).
Joseph et al. Nuclear Med Comm 9, 763–769 (1988).
Queen et al. PNAS. (vol. 86) 10029, 1989.
Huse (Antibody Engineering) Borrebaeck 1992 p. 103.
Emery et al. Exp. Opin Invest Drugs 3(3) 241–25 1994.
Cunningham et al. TibTech Apr. 1992 vol. 10 (4) 112–113.
Ward (Antibody Engineering) Borrebaeck ed. 1992. p. 121.
Wu and Kabat, "Sequences of Proteins of Immunological Interest," U.S. Department of Health and Human Services (1991), pp. 104, 243 and 318.
"The Three–Dimensional Structure of the Fab' Fragment of a Human Myeloma Immunoglobulin at 2.0–A Resolution"—Poljak, et al., Proc. Nat. Acad. Sci. USA 71(9): 3440–3444 (1974).
"Evolution of Human Immunoglobulin κ J Region Genes*", Hieter, et al. The Journal of Biological Chemistry, 257(3): 1516–1522 (1982).
"Glucocorticoids regulate expression of dihydrofolate reductase cDNA in mouse mammary tumour virus chimaeric plasmids", Lee et al., Nature 294: 228–232 (1981).
"Production of functional chimaeric mouse/human antibody" Boulianne et al. Nature 312:643–646 (1984).
"Immunohistochemical Localization and Molecular Characteristics of Three Monoclonal Antibody–Defined Epitopes Detectable on Carcinoembryonic Antigen (CEA)", Bosslet et al., Int. J. Cancer 36:75–84 (1985).
"Replacing the complementarity–determining regions in a human antibody with those from a mouse", Jones et al., Nature, 321: 522–525 (1986).
"A monoclonal antibody with binding and inhibiting activity towards human pancreatic carcinoma cells", Bosslet et al., Cancer Immunol Immunother 23:185–191 (1986).
"The Immunogenicity of Chimeric Antibodies", Brueggemann, et al., J. Exp. Med. 170:2153–2157 (1989).
"A Novel Approach To Tc–99m–Labeled Monoclonal Antibodies", Schwarz et al., J. Nucl. Med. 28(4):721 (1987).
"Reshaping Human Antibodies: Grafting an Antilysozyme Activity", Verhoeyen et al., Science, 239:1534–1536 (1988).
"Reshaping human antibodies for therapy", Riechmann et al., Nature 332(6162): 323–327 (1988).

*Primary Examiner*—Lila Feisee
*Assistant Examiner*—John Lucas
*Attorney, Agent, or Firm*—Finnegan, Henderson, Farabow, Garrett & Dunner, L.L.P.

[57] ABSTRACT

The present invention describes granulocyte-binding antibody constructs, which were derived from the monoclonal mouse antibody MAk BW 250/183 (EP-A1-0 388 914), as well as a process for their preparation and their use.

13 Claims, 1 Drawing Sheet

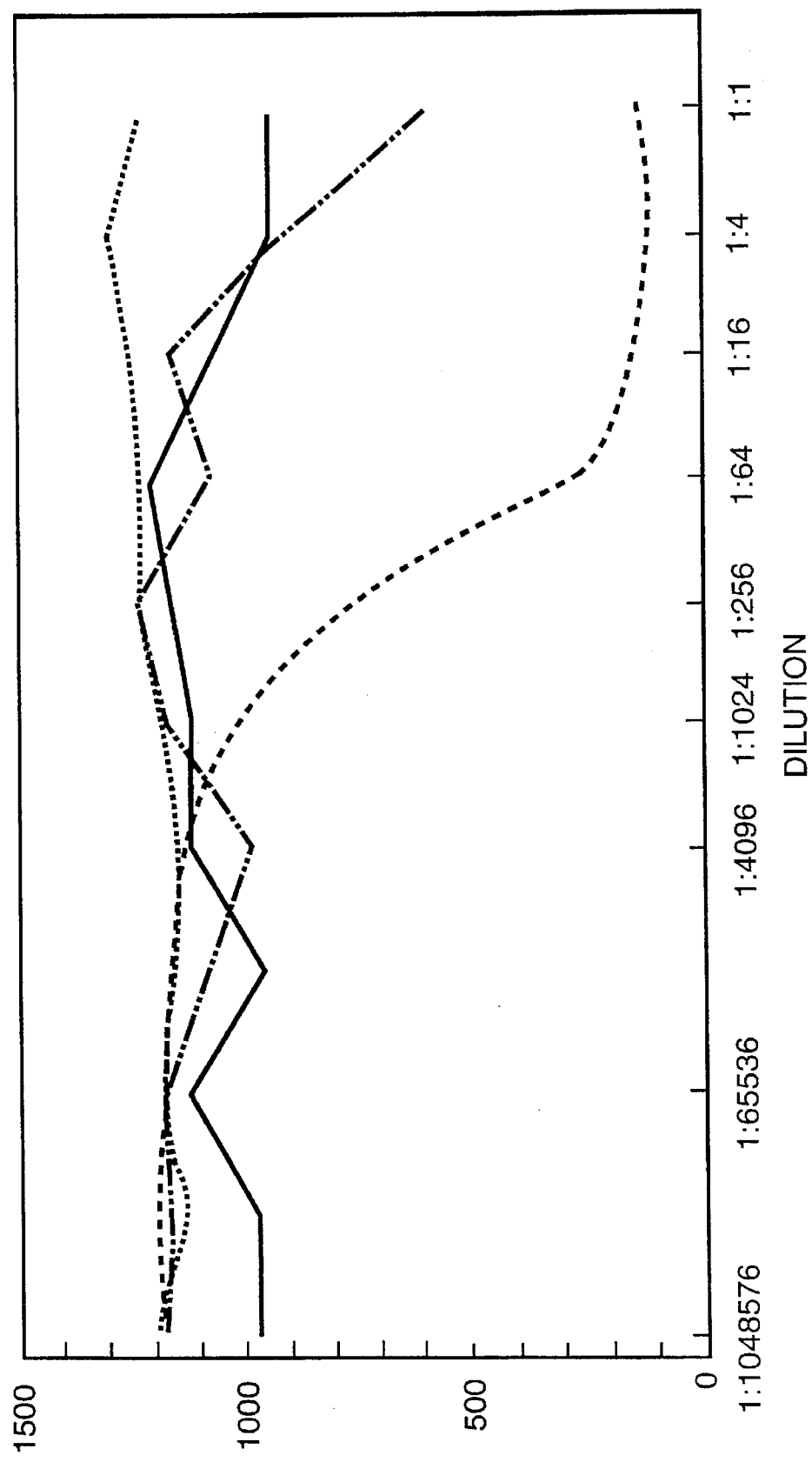

GRANULOCYTE-BINDING ANTIBODY CONSTRUCTS, THEIR PREPARATION AND USE

This application is a continuation of application Ser. No. 08/100,963, filed Aug. 3, 1993, now abandoned.

BACKGROUND OF THE INVENTION

The present invention describes granulocyte-binding antibody constructs, which were derived from the monoclonal mouse antibody Mab BW 250/183 (EP-A1-0 388 914), as well as a process for their preparation and their use.

The monoclonal antibody Mab BW 250/183 is a monoclonal mouse antibody of the IgG1 kappa type which is directed against the "nonspecific crossreacting antigen" (NCA)95 and against the carcinoembryonic antigen (CEA) and does not have any unwanted cross reactions with normal human tissues apart from the colon mucosa. Its binding to granulocytes and granulocyte precursors in the bone marrow also makes a therapeutic application possible.

Usually, antibodies which were isolated from rodents, in particular mice, are used in the therapeutic application of monoclonal antibodies (Mabs) in humans. However, the repeated administration of high doses of antibodies of non-human (xenogenic) origin can lead to an immune reaction in the patients. After about 10–14 days they develop anti-mouse immunoglobulin antibodies (HAMAs). A therapy of this nature must therefore be discontinued after 10 days and cannot be reinitiated.

In the meantime, success has been achieved, with the aid of molecular biological methods, in altering the xenogeneic antibodies in such a way that they are either no longer or only very weakly immunogenic for humans but nevertheless preserve their antigen-binding properties. To do this, the constant exons ($CH_1$, H, $CH_2$, $CH_3$, CL) in the genes encoding the H and L chains of the xenogeneic Mabs were exchanged, in a first step, for exons from human immunoglobin genes (Boulianne, G. L., Nobumichi Hozumi, and Marc J. Shulman (1984) Nature 321, 643–646). In this way, so-called chimeric antibodies are obtained which are composed of variable domains of xenogeneic origin and human constant regions. These chimeric antibodies still contain about 30% of xenogeneic protein sequences so that when they are used in immunotherapy an immune reaction, even if weaker, is still to be expected in the patients (Brüggemann, M., Greg Winter, Herman Waldmann, and Michael S. Neuberger (1989) J. Exp. Med. 170, 2153–2157).

In order to reduce the immunogenicity of xenogeneic antibodies still further, a technique was developed by G. Winter and M. Neuberger (1986) in which only the CDR loops of the $V_L$ and $V_H$ domains of the xenogenic antibodies are transferred to $V_L$ and $V_H$ domains of human antibodies (Jones, P. T., Paul H. Dear, Jefferson Foote, Michael S. Neuberger, and Greg Winter (1986) Nature 321,522–525), a process which is termed "humanization" and takes place at the level of the $V_H$ and $V_L$ genes. The structural variability of the $V_H$ and $V_L$ domains is in general confined to the CDR loops ["CDR" stands for complementarity-determining regions].

In the present patent application, antibody chains are now described which are specific for human granulocytes and in which at least the CDR regions of the heavy and light chains derive from the mouse Mab BW 250/183 (EP-A1-0 388 914). The remaining parts of molecular constructs prepared thereby, e.g. monoclonal antibodies, are preferably derived from human antibodies.

BRIEF DESCRIPTION OF THE DRAWINGS

FIG. 1 depicts a competition assay using Mabs BW 250/183, 431/26, 494/32, and 374/14.

DETAILED DESCRIPTION OF THE INVENTION

In general, the essential steps in the humanization of an antibody are: the cloning and nucleic acid sequence analysis of the specific $V_H$ and $V_L$ genes, the computer-assisted design of the synthetic oligonucleotides for the transfer of the CDR loops to the human $V_H$ and $V_L$ domains and the transfer of the CDR loops to the human $V_H$ and $V_L$ domains by means of specific mutagenesis (Riechmann, L., Michael Clark, Herman Waldmann, and Greg Winter (1988) Nature 332, 323–327; Verhoeyen, M., Cesar Milstein, and Greg Winter (1988) Science 239, 1534–1536).

In the first instance, humanizing the Mab BW 250/183 according to the process described by Riechmann and Verhoeyen led to a humMab which has a reduced antigen binding affinity as compared with the murine Mab BW 250/183. Surprisingly, however, exchange of an additional amino acid in the $V_L$ domain led to a humMab which has an antigen binding affinity similar to that of the mouse Mab BW 250/183.

The invention therefore relates to an antibody light chain containing a polypeptide having the amino acid sequence given in Table 1c (SEQ ID No:17) and to an antibody heavy chain containing a peptide having the amino acid sequence given in Table 1a (SEQ ID No:12), as well as to their functionally equivalent variants. For the purposes of the invention, functionally equivalent variants are in general understood to mean those variants of the antibody light and heavy chains according to the invention which bind to human granulocytes and granulocyte precursors, and to NCA 95 and CEA, but not to normal human tissues, with the exception of the colon mucosa, in which the amino acid in position 46 (proline) in the antibody light chain must not be exchanged for another amino acid.

In addition, for the purposes of the invention, functionally equivalent variants are understood to mean those variants of the antibody light and heavy chains according to the invention in which, at amino acid positions which do not participate directly in the antigen binding, amino acid exchanges may be made which do not lead to structural changes in the domain structures and consequently neither to impairment of the antigen binding properties.

These amino acid exchanges can be located in the CDRs and in the framework regions of the variable domains. These exchanges can, e.g., be conservative exchanges with regard to size, polarity and charge of the amino acid side chains within and outside of the CDRs. The exchanges can, e.g., be between the following amino acid pairs, as has also been described for the most part in Güssow and Seemann: Phe/Tyr; Leu/Met; Val/Ile; Gln/His; Asp/Glu; Arg/Lys; Trp/Arg; Asn/Asp; Gly/Ala; Ser/Thr; Gln/Asp; Gln/Glu; Asn/Glu; His/Arg; His/Asn; Ile/Leu; Ile/Met; Leu/Phe; Leu/Val; Val/Met.

These exchanges may also be nonconservative or arbitrary exchanges outside of the CDRs, which do not impair the structure of the domains and the folding of the CDRs, or the interactions between VH and VL domains.

The invention furthermore relates to a molecular construct containing at least one of the antibody chains according to the invention and at least one further amino acid chain, which is linked to the antibody chain and which is different from the antibody chain according to the invention.

The invention additionally relates to a molecular construct comprising the antibody chain according to Table 1a or 1c (SEQ ID Nos:12 or 17) and further amino acid chains linked to the said sequences, where these amino acid chains are different from the antibody chains according to the invention and are preferably parts of a human antibody, for example parts of the constant regions of the heavy and light chains.

Special embodiments of these molecular constructs are, for example, a single domain fragment or a single chain fragment. In this context, a single domain fragment is understood to mean a construct containing a single antibody variable domain, according to the invention, and a single chain fragment is understood to mean a construct containing an antibody heavy chain and an antibody light chain according to the invention, which chains are linked to each other via a linker.

The present invention also relates to humanized monoclonal antibodies (humMab), or functionally active parts thereof, which contain the light and heavy antibody chain according to the invention. A functionally active part thereof is, for example, a F(ab) or F(ab') fragment whose hinge region is coded for by one or more hinge exons.

In addition, the molecular constructs according to the invention or the humMab effector molecules according to the invention can contain, for example, a chelating agent (e.g. EDTA, DTPA) for complexing metal ions, a toxin (e.g. ricine), a second binding region of different specificity or having catalytic properties, or an enzyme. All enzymes which are not present in the human organism, such as, for example, β-lactamase or carboxypeptidase, are preferred as enzymes. Of the enzymes present in the human organism, those enzymes can generally be used which are present extracellularly, preferably in low concentrations, such as, for example, all lysosomal glucuronidases or all sialidases, preferably the human sialidase which modifies the sialyl Lew$^x$ epitope to Lew$^x$. The sialidase is particularly advantageous in the treatment of diseases which are associated with altered granulocyte function, such as, e.g., sepsis. By means of desialylating the sialyl Lew$^x$ epitope, interaction of activated granulocytes with the vascular endothelium is prevented, resulting in impairment of granulocyte migration out of the blood vessel system. In this way, the inflammatory process, which takes place extravascularly, is reduced or blocked. The constructs according to the invention or the humMabs according to the invention can be labeled with TC-99m according to the method of Schwarz (Schwarz, A. & Steinsträsser, A. (1987), A novel approach to TC-99 labelled monoclonal antibodies. J. Nucl. Med., 28, 721), for example, or with Re or Y according to well-known methods. In general, the invention also includes any other desired labeling with alpha, beta or gamma emitters.

The linking of the antibody chains according to the invention to effector molecules can be carried out according to well-known processes either chemically or using the methods of gene technology. The antibody chains according to the invention, themselves, can likewise be prepared chemically or by gene technology. In the latter case, if the molecular construct, e.g. a humMab, comprises a Fab or F(ab')$_2$ fragment rather than an intact antibody molecule, the 3' regulatory sequences (stop codon, 3' nontranslated regions and poly-A addition signal), which are lost with the removal of the constant part of the immunoglobulin gene, are replaced, during construction of the genes for the heavy chains, by the C3 Exon, the 3' non-translated region and the poly-A addition signal of a human MHC Class I gene, preferably an HLA B27 gene.

In general, the host cell can, within the scope of the preparation by gene technology of the antibody chains or the molecular constructs according to the invention, be transfected with one or more vector(s). One vector contains, for example, an operon which encodes a polypeptide derived from an antibody light chain, and a second vector contains, for example, an operon which encodes a polypeptide derived from an antibody heavy chain. In this example, the two vectors are preferably identical, except for the regions encoding the light and heavy chains, in order to ensure, as far as possible, equally good expression of the light and heavy chains. Additional vectors generally contain selectable markers.

Alternatively, a vector can also be used for transfecting the host cell which contains, for example, both the DNA sequences encoding the light chain and those encoding the heavy chain.

The DNA sequences which encode the light and heavy chains are composed either of genomic sequences or of the cDNA sequences, or of a mixture of the two. Preferably, the said DNA sequences are composed, at least in part, of genomic DNA.

The host cell which is used for expressing the antibody chain(s) according to the invention and the molecular construct(s) according to the invention is preferably a eucaryotic cell, in particular a mammalian cell, such as, for example, a BHK cell, a CHO cell or a myeloid cell.

The present invention therefore also relates, additionally, to cloning and expression vectors and to transfected cells. The invention moreover includes therapeutic and diagnostic formulations which contain the constructs according to the invention, and their preparation, as well as the use of such formulations in the therapy and diagnosis of diseases, preferably inflammations, or tumors which are metastasizing into the bone marrow, in particular carcinoma of the breast, lymphoma, carcinoma of the prostate or small-cell lung carcinoma.

The general methods by which the vectors can be constructed, and the transfection technology and the cell culture technology, are known to the person skilled in the art and are described, for example, by Maniatis (Sambrook, Fritsch, Maniatis; Molecular Cloning, A Laboratory Manual; Cold Spring Harbor Laboratory, pp. 11–44, 51–127, 133–134, 141, 146, 150–167, 170, 188–193, 197–199, 248–255, 270–294, 310–328, 364–401, 437–506 (1982); Sambrook, Fritsch, Maniatis; Molecular Cloning, A Laboratory Manual, Second Edition; Cold Spring Harbor Press, pp. 16.2–16.22, 16.30–16.40, 16.54–16.55 (1989)). The present invention is now described in detail using examples and by means of the claims.

EXAMPLE 1

The V gene sequences of the mouse Mab BW 250/183 are described in EP-A1-388 914 (Mab A):

VH (SEQ ID NO: 1 contains 357 base pairs and SEQ ID NO: 2 contains the corresponding 119 amino acids)

| CAG | GTC | CAA | CTG | CAG | GAG | TCT | GGA | GGA | GGC | TTG | GTA | CAG | CCT |
|---|---|---|---|---|---|---|---|---|---|---|---|---|---|
| Gln | Val | Gln | Leu | Gln 5 | Glu | Ser | Gly | Gly | Gly 10 | Leu | Val | Gln | Pro |

| GGG | GGT | TCT | CTG | AGA | CTC | TCC | TGC | GCA | ACT | TCT | GGG | TTC | AGT |
|---|---|---|---|---|---|---|---|---|---|---|---|---|---|
| Gly 15 | Gly | Ser | Leu | Arg | Leu 20 | Ser | Cys | Ala | Thr | Ser 25 | Gly | Phe | Ser 30 |

| GAT | TAC | TAC | ATG | AAC | TGG | GTC | CGC | CAG | CCT | CCA | GGA | AAA | GCA |
|---|---|---|---|---|---|---|---|---|---|---|---|---|---|
| Asp | Tyr | Tyr | Met | Asn 35 | Trp | Val | Arg | Gln | Pro 40 | Pro | Gly | Lys | Ala |

| CTT | GAG | TGG | TTG | GGT | TTT | ATT | TCA | AAC | AAA | CCT | AAT | GGG | CAC |
|---|---|---|---|---|---|---|---|---|---|---|---|---|---|
| Leu 45 | Glu | Trp | Leu | Gly | Phe 50 | Ile | Ser | Asn | Lys | Pro | Asn | Gly | His 55 |

| ACA | ACA | GAG | TAC | AGT | GCA | TCT | GTG | AAG | GGT | CGG | TTC | ACC | ATC |
|---|---|---|---|---|---|---|---|---|---|---|---|---|---|
| Thr | Thr | Glu | Tyr | Ser 60 | Ala | Ser | Val | Lys | Gly 65 | Arg | Phe | Thr | Ile |

| TCC | AGA | GAT | AAT | TCC | CAA | AGC | ATC | CTC | TAT | CTT | CAA | ATG | AAC |
|---|---|---|---|---|---|---|---|---|---|---|---|---|---|
| Ser 70 | Arg | Asp | Asn | Ser | Gln 75 | Ser | Ile | Leu | Tyr | Leu 80 | Gln | Met | Asn |

| ACC | CTG | AGA | GCT | GAG | GAC | AGT | GCC | ACT | TAT | TAT | TGT | GCA | AGA |
|---|---|---|---|---|---|---|---|---|---|---|---|---|---|
| Thr | Leu | Arg | Ala | Glu 85 | Asp | Ser | Ala | Thr | Tyr | Tyr 90 | Cys | Ala | Arg |

| GAT | AAG | GGA | ATA | CGA | TGG | TAC | TTC | GAT | GTC | TGG | GGC | CAA | GGG |
|---|---|---|---|---|---|---|---|---|---|---|---|---|---|
| Asp 95 | Lys | Gly | Ile | Arg | Trp 100 | Tyr | Phe | Asp | Val | Trp | Gly | Gln | Gly 105 |

| ACC | ACG | GTC | ACC | GTC | TCC | TCA |
|---|---|---|---|---|---|---|
| Thr | Thr | Val | Thr 110 | Val | Ser | Ser |

The amino acid positions are numbered in the Sequence Listing found immediately prior to the claims, according to Wu and Kabat, "Sequences of Proteins of Immunological Interest", U.S. Department of Health and Human Services".

VK (SEQ ID NO: 3 contains 315 base pairs and SEQ ID NO: 4 contains the corresponding 105 amino acids)

| GAC | ATT | CAG | CTG | ACC | CAG | TCT | CCA | GCA | ATC | CTG | TCT | GCA | TCT |
|---|---|---|---|---|---|---|---|---|---|---|---|---|---|
| Asp | Ile | Gln | Leu | Thr 5 | Gln | Ser | Pro | Ala | Ile 10 | Leu | Ser | Ala | Ser |

| CCA | GGG | GAG | AAG | GTC | ACA | ATG | ACT | TGC | AGG | GCC | AGC | TCA | AGT |
|---|---|---|---|---|---|---|---|---|---|---|---|---|---|
| Pro 15 | Gly | Glu | Lys | Val | Thr 20 | Met | Thr | Cys | Arg | Ala 25 | Ser | Ser | Ser |

| GTA | AGT | TAC | ATG | CAC | TGG | TAC | CAG | CAG | AAG | CCA | GGA | TCC | TCC |
|---|---|---|---|---|---|---|---|---|---|---|---|---|---|
| Val | Ser | Tyr | Met | His 35 | Trp | Tyr | Gln | Gln | Lys | Pro 40 | Gly | Ser | Ser |

| CCC | AAA | CCC | TGG | ATT | TAT | GCC | ACA | TCC | AAC | CTG | GCT | TCT | GGA |
|---|---|---|---|---|---|---|---|---|---|---|---|---|---|
| Pro | Lys 45 | Pro | Trp | Ile | Tyr | Ala 50 | Thr | Ser | Asn | Leu | Ala 55 | Ser | Gly |

| GTC | CCT | GCT | CGC | TTC | AGT | GGC | AGT | GGG | TCT | GGG | ACC | TCT | TAC |
|---|---|---|---|---|---|---|---|---|---|---|---|---|---|
| Val | Pro | Ala 60 | Arg | Phe | Ser | Gly | Ser 65 | Gly | Ser | Gly | Thr | Ser 70 | Tyr |

| TCT | CTC | ACA | ATC | ATC | AGA | GTG | GAG | GCT | GAA | GAT | GCT | GCC | ACT |
|---|---|---|---|---|---|---|---|---|---|---|---|---|---|
| Ser | Leu | Thr | Ile 75 | Ile | Arg | Val | Trp | Ala 80 | Glu | Asp | Ala | Ala | Thr 85 |

| TAT | TAC | TGC | CAG | CAG | TGG | AGT | AGT | AAC | CCG | CTC | ACG | TTC | GGT |
|---|---|---|---|---|---|---|---|---|---|---|---|---|---|
| Tyr | Tyr | Cys | Gln | Gln 90 | Trp | Ser | Ser | Asn | Pro 95 | Leu | Thr | Phe | Gly |

| GCT | GGG | ACC | AAG | CTG | GAG | ATC |
|---|---|---|---|---|---|---|
| Ala 100 | Gly | Thr | Lys | Leu | Glu 105 | Ile |

The myeloma proteins NEW ($V_H$) and REI ($V_L$) were used as human acceptor V domains (Poljak, R. J., Amzel, L. M., Chen, B. L., Phizackerley, R. P., Saul, F. (1974) Proc. Natl. Acad. Sci. USA 71, 3440–3444; Palm, W., Hilschmann, N. (1973) Z. Physiol. Chem. 354, 1651–1654; Palm, W., Hilschmann, N. (1975) Z. Physiol. Chem. 356, 167–191). In designing the oligonucleotides for transplanting the CDR regions of the Mab BW 250/183 to the human acceptor V domains, the procedure was as described by Riechmann, L., Michael Clark, Herman Waldmann, and Greg Winter (Nature 332, 323–327, 1988):

The humanization was carried out according to the method described by L. Riechmann et al. and Güssow and Seemann (Methods in Enzymology, 203, 99–121, 1991), with, in the heavy chain, in addition to the CDR regions (Tramontano, A., Chothia, C., Lesk, A. M. (1990) J. Mol. Biol. 215, 175–182), the amino acid position 27 in NEW being changed from Ser to Phe, the amino acid positions 28 NEW and 29 NEW being deleted, and the position 71 NEW being changed from Val to Arg.

From this, the following oligonucleotides for specific mutagenesis result:

250/183 Vk CDR1 (SEQ ID NO: 5):

5' CTG CTG GTA CCA GTG CAT GTA ACT TAC ACT TGA GCT
GGC CCT ACA GGT GAT GGT 3'

250/183 Vk CDR2 (SEQ ID NO: 6):

5' GCT TGG CAC ACC AGA AGC CAG GTT GGA TGT GGC GTA
GAT CAG CAG 3'

250/183 Vk CDR3 (SEQ ID NO: 7):

5' CCC TTG GCC GAA CGT GAG CGG GTT ACT ACT CCA CTG
CTG GCA GTA GTA GGT 3'

250/183 VH CDR1 (SEQ ID NO: 8):

5' CTG TCT CAC CCA GTT CAT GTA GTA ATC GCT GAA GCC
AGA CAC GTT 3'

250/183 VH CDR2 (SEQ ID NO: 9):

5' CTT GCT GGT GTC TCT GAG CAT TGT CAC TCT ACC CTT
CAC GGA TGC GCT GTA CTC GGT TGT GTG TCC GTT AGG
CTT GTT TGA AAT AAA TCC AAT CCA CTC 3'

250/183 VH CDR3 (SEQ ID NO: 10:

5' GCC TGG ACC CCA GAC ATC GAA GTA CCA TCG TAT TCC
CTT ATC TCT TGC ACA ATA 3'

The $V_H$ and $V_K$ genes of the humanized anti-lysozyme antibody D1-3 (Verhoeyen, M., Michael, Clark, Herman Waldmann, Greg Winter (1988), Nature 332, 323–327) were used for the mutageneses. This resulted in the sequences, depicted in Tab. 1a and 1b (SEQ ID Nos:11–14), of the first humanized versions of the $V_H$ and $V_K$ genes of Mab 250/183.

TABLE 1a

250 VH hum

| CAG | GTC | CAA | CTG | CAG | GAG | AGC | GGT | CCA | GGT | CTT | GTG | AGA | CCT |
|---|---|---|---|---|---|---|---|---|---|---|---|---|---|
| Gln | Val | Gln | Leu | Glu | Glu | Ser | Gly | Pro | Gly | Leu | Val | Arg | Pro |
|  |  |  |  | 5 |  |  |  |  | 10 |  |  |  |  |

| AGC | CAG | ACC | CTG | AGC | CTG | ACC | TGC | ACC | GTG | TCT | GGC | TTC | AGC |
|---|---|---|---|---|---|---|---|---|---|---|---|---|---|
| Ser | Gln | Thr | Leu | Ser | Leu | Thr | Cys | Thr | Val | Ser | Gly | Phe | Ser |
| 15 |  |  |  |  | 20 |  |  |  |  | 25 |  |  |  |

| GAT | TAC | TAC | ATG | AAC | TGG | GTG | AGA | CAG | CCA | CCT | GGA | CGA | GGT |
|---|---|---|---|---|---|---|---|---|---|---|---|---|---|
| Asp | Tyr | Tyr | Met | Asn | Trp | Val | Arg | Gln | Pro | Pro | Gly | Arg | Gly |
|  |  | 30 |  |  | 35 |  |  |  |  | 40 |  |  |  |

| CTT | GAG | TGG | ATT | GGA | TTT | ATT | TCA | AAC | AAA | CCT | AAT | GGT | CAC |
|---|---|---|---|---|---|---|---|---|---|---|---|---|---|
| Leu | Glu | Trp | Ile | Gly | Phe | Ile | Ser | Asn | Lys | Pro | Asn | Gly | His |
| 45 |  |  |  |  | 50 |  |  |  |  |  |  |  | 55 |

| ACA | ACA | GAG | TAC | AGT | GCA | TCT | GTG | AAG | GGT | AGA | GTG | ACA | ATG |
|---|---|---|---|---|---|---|---|---|---|---|---|---|---|
| Thr | Thr | Glu | Tyr | Ser | Ala | Ser | Val | Lys | Gly | Arg | Val | Thr | Met |
|  |  |  |  | 60 |  |  |  |  | 65 |  |  |  |  |

| CTG | CGA | GAC | ACC | AGC | AAG | AAC | CAG | TTC | AGC | CTG | AGA | CTC | AGC |
|---|---|---|---|---|---|---|---|---|---|---|---|---|---|
| Leu | Arg | Asp | Thr | Ser | Lys | Asn | Gln | Phe | Ser | Leu | Arg | Leu | Ser |
| 70 |  |  |  |  | 75 |  |  |  |  | 80 |  |  |  |

| AGC | GTG | ACA | GCC | GCC | GAC | ACC | GCG | GTC | TAT | TAT | TGT | GCA | AGA |
|---|---|---|---|---|---|---|---|---|---|---|---|---|---|
| Ser | Val | Thr | Ala | Ala | Asp | Thr | Ala | Val | Tyr | Tyr | Cys | Ala | Arg |
|  |  |  |  | 85 |  |  |  |  | 90 |  |  |  |  |

| GAT | AAG | GGA | ATA | CGA | TGG | TAC | TTC | GAT | GTC | TGG | GGT | CAA | GGC |
|---|---|---|---|---|---|---|---|---|---|---|---|---|---|
| Asp | Lys | Gly | Ile | Arg | Trp | Tyr | Phe | Asp | Val | Trp | Gly | Gln | Gly |
| 95 |  |  |  |  | 100 |  |  |  |  |  |  | 105 |  |

| AGC | CTC | GTC | ACA | GTC | TCC | TCA |
|---|---|---|---|---|---|---|
| Ser | Leu | Val | Thr | Val | Ser | Ser |
|  |  |  | 110 |  |  |  |

TABLE 1b

250 Vk hum (SEQ ID NO: 13 contains 321 base pairs and SEQ ID NO: 14 contains the corresponding 107 amino acids)

| GAC | ATC | CAG | ATG | ACC | CAG | AGC | CCA | AGC | AGC | CTG | AGC | GCC | AGC |
|---|---|---|---|---|---|---|---|---|---|---|---|---|---|
| Asp | Ile | Gln | Met | Thr | Gln | Ser | Pro | Ser | Ser | Leu | Ser | Ala | Ser |
| 1 |  |  |  | 5 |  |  |  |  | 10 |  |  |  |  |

| GTG | GGT | GAC | AGA | GTG | ACC | ATC | ACC | TGT | AGG | GCC | AGC | TCA | AGT |
|---|---|---|---|---|---|---|---|---|---|---|---|---|---|
| Val | Gly | Asp | Arg | Val | Thr | Ile | Thr | Cys | Arg | Ala | Ser | Ser | Ser |
| 15 |  |  |  |  | 20 |  |  |  |  | 25 |  |  |  |

| GTA | AGT | TAC | ATG | CAC | TGG | TAC | CAG | CAG | AAG | CCA | GGT | AAG | GCT |
|---|---|---|---|---|---|---|---|---|---|---|---|---|---|
| Val | Ser | Tyr | Met | His | Trp | Tyr | Gln | Gln | Lys | Pro | Gly | Lys | Ala |
| 30 |  |  |  |  | 35 |  |  |  |  | 40 |  |  |  |

| CCA | AAG | CTG | CTG | ATC | TAC | GCC | ACA | TCC | AAC | CTG | GCT | TCT | GGT |
|---|---|---|---|---|---|---|---|---|---|---|---|---|---|
| Pro | Lys | Leu | Leu | Ile | Tyr | Ala | Thr | Ser | Asn | Leu | Ala | Ser | Gly |
|  | 45 |  |  |  |  | 50 |  |  |  |  | 55 |  |  |

| GTG | CCA | AGC | AGA | TTC | AGC | GGT | AGC | GGT | AGC | GGT | ACC | GAC | TTC |
|---|---|---|---|---|---|---|---|---|---|---|---|---|---|
| Val | Pro | Ser | Arg | Phe | Ser | Gly | Ser | Gly | Ser | Gly | Thr | Asp | Phe |
|  |  | 60 |  |  |  |  | 65 |  |  |  |  | 70 |  |

| ACC | TTC | ACC | ATC | AGC | AGC | CTC | CAG | CCA | GAG | GAC | ATC | GCC | ACC |
|---|---|---|---|---|---|---|---|---|---|---|---|---|---|
| Thr | Phe | Thr | Ile | Ser | Ser | Leu | Gln | Pro | Glu | Asp | Ile | Ala | Thr |
|  |  |  | 75 |  |  |  |  | 80 |  |  |  |  | 85 |

| TAC | TAC | TGC | CAG | CAG | TGG | AGT | AGT | AAC | CCG | CTC | ACG | TTC | GGC |
|---|---|---|---|---|---|---|---|---|---|---|---|---|---|
| Tyr | Tyr | Cys | Gln | Gln | Trp | Ser | Ser | Asn | Pro | Leu | Thr | Phe | Gly |
|  |  |  |  |  | 90 |  |  |  |  | 95 |  |  |  |

| CAA | GGG | ACC | AAG | GTG | GAA | ATC | AAA | CGT |
|---|---|---|---|---|---|---|---|---|
| Gln | Gly | Thr | Lys | Val | Glu | Ile | Lys | Arg |
| 100 |  |  |  |  | 105 |  |  |  |

The humanized $V_H$ and $V_L$ genes were cloned in expression vectors which contain the human IgG3 gene (DE-A1-3825615) and the human $C_K$ gene (Hieter, P. A., Maizel, J. V., Leder, P. (1982), J. Biol. Chem. 257, 1516–1522), and, together with suitable plasmids carrying selection markers, such as, e.g., pRMH140 (Hudziak, R. M., Laski, F. A., RajBhandary, U. L., Sharp, P. A., Capecchi, M. R. (1982) Cell 31, 137–146) or pSV2 dhfr (Lee, F., Mulligan, R., Berg, P., Ringold, G. (1981) Nature 294, 228), transfected into mammalian cells (Wirth, M., Bode, J., Zettlmeißl, G., Hauser, H. (1988) Gene 73, 419–426).

However, characterization of this first version of the humanized antibody (according to Example 2) indicated a strongly reduced affinity for the antigen as compared with that of the mouse Mab.

In a new mutagenesis of the amino acid sequences, in addition to the CDRs, the amino acid position REI 46 in the $V_L$ domain was changed from Leu to Pro. This resulted in the following oligonucleotide (250/183 $V_K$ CDR2new) for mutagenizing the CDR2 of the first version of the humanized 250/183 $V_K$ gene:

EXAMPLE 2

Immunological examination of BW 250/183 hum

Supernatants from BHK cells, which had been transfected with the DNA constructs of the second version of the hum 250/183, were tested for their content of humMab and for the specificity of the humMab.

For this purpose, 2 different ELISA tests were employed:
a) ELISA for determining human IgG concentration
b) Epitope competition ELISA on solid-phase antigen ve a) The ELISA for determining human IgG concentration was carried out in accordance with the method described in Johannson et al. (J. Immunol. Methods 87, 7–11).

To serve as the solid-phase antibody, a goat anti-human IgG (Southern Biotechnology Associates (order No. 2040-01)) was diluted 1:300. An alkaline phosphatase-labeled goat anti-human kappa antibody from the same firm (order No.: 2060-04), which was employed at a dilution of 1:250, served as the detection antibody.

ve b) The epitope competition ELISA was likewise carried out as described in Johannson et al. (see above).

250/183 Vk CDR2 new (SEQ ID NO: 15):

5' GCT TGG CAC ACC AGA AGC CAG GTT GGA TGT GGC GTA

GAT CAG CGG CTT TGG AGC CTT 3'

The sequence of the second version of the humanized light chain V gene, resulting from this mutagenesis, is depicted in Table 1c.

However, the polystyrene plates were coated with 75 μl of CEA at a concentration of 15 μg/ml. Equal volumes of different concentrations (consecutively dilutions 1:2)

TABLE 1c

250 VK hum (SEQ ID NO: 16 contains 321 base pairs and SEQ ID NO: 17 contains the corresponding 107 amino acids)

| GAC | ATC | CAG | ATG | ACC | CAG | AGC | CCA | AGC | AGC | CTG | AGC | GCC | AGC |
|---|---|---|---|---|---|---|---|---|---|---|---|---|---|
| Asp | Ile | Gln | Met | Thr | Gln | Ser | Pro | Ser | Ser | Leu | Ser | Ala | Ser |
| 1 | | | | 5 | | | | | 10 | | | | |

| GTG | GGT | GAC | AGA | GTG | ACC | ATC | ACC | TGT | AGG | GCC | AGC | TCA | AGT |
|---|---|---|---|---|---|---|---|---|---|---|---|---|---|
| Val | Gly | Asp | Arg | Val | Thr | Ile | Thr | Cys | Arg | Ala | Ser | Ser | Ser |
| 15 | | | | | 20 | | | | | 25 | | | |

| GTA | AGT | TAC | ATG | CAC | TGG | TAC | CAG | CAG | AAG | CCA | GGT | AAG | GCT |
|---|---|---|---|---|---|---|---|---|---|---|---|---|---|
| Val | Ser | Tyr | Met | His | Trp | Tyr | Gln | Gln | Lys | Pro | Gly | Lys | Ala |
| 30 | | | | | 35 | | | | | 40 | | | |

| CCA | AAG | CCG | CTG | ATC | TAC | GCC | ACA | TCC | AAC | CTG | GCT | TCT | GGT |
|---|---|---|---|---|---|---|---|---|---|---|---|---|---|
| Pro | Lys | Pro | Leu | Ile | Tyr | Ala | Thr | Ser | Asn | Leu | Ala | Ser | Gly |
| | 45 | | | | | 50 | | | | | 55 | | |

| GTG | CCA | AGC | AGA | TTC | AGC | GGT | AGC | GGT | AGC | GGT | ACC | GAC | TTC |
|---|---|---|---|---|---|---|---|---|---|---|---|---|---|
| Val | Pro | Ser | Arg | Phe | Ser | Gly | Ser | Gly | Ser | Gly | Thr | Asp | Phe |
| | | 60 | | | | | 65 | | | | | 70 | |

| ACC | TTC | ACC | ATC | AGC | AGC | CTC | CAG | CCA | GAG | GAC | ATC | GCC | ACC |
|---|---|---|---|---|---|---|---|---|---|---|---|---|---|
| Thr | Phe | Thr | Ile | Ser | Ser | Leu | Gln | Pro | Glu | Asp | Ile | Ala | Thr |
| | | | 75 | | | | | 80 | | | | | 85 |

| TAC | TAC | TGC | CAG | CAG | TGG | AGT | AGT | AAC | CCG | CTC | ACG | TTC | GGC |
|---|---|---|---|---|---|---|---|---|---|---|---|---|---|
| Tyr | Tyr | Cys | Gln | Gln | Trp | Ser | Ser | Asn | Pro | Leu | Thr | Phe | Gly |
| | | | | 90 | | | | | 95 | | | | |

| CAA | GGG | ACC | AAG | GTG | GAA | ATC | AAA | CGT |
|---|---|---|---|---|---|---|---|---|
| Gln | Gly | Thr | Lys | Val | Glu | Ile | Lys | Arg |
| 100 | | | | | 105 | | | | of the murine competitors were added to the transfectant supernatant, which contained 200 ng/ml of hum 250/183, and the mixtures incubated at room temperature for 15 minutes. Subsequently, each mixture was added to the CEA solid phase and the plates were incubated at room temperature for 20 hours, and the CEA-bound hum 250/183 was detected using a 1:250 diluted goat anti-human kappa antibody labeled with alkaline phosphatase (order No.: 2060-04)from Southern Biotechnology Associates.

RESULT

Using the ELISAs for detecting human IgG, it was possible to find supernatants from transfected BHK cells which contained about 200 ng/ml of human IgG. These supernatants were then examined for their specificity in an epitope competition ELISA.

The FIGURE shows that, of the murine Mabs employed in excess for the competition, only the Mab BW 250/183 inhibits, in a dose dependent manner, binding of the hum 250/183 to its CEA-NCA95 specific epitope, which was attached to the solid phase. The Mabs BW 431/26 and BW 374/14, which recognize other epitopes on CEA (Bosslet, K., et al., Int. J. Cancer 36, 75–84, 1985; see above), do not have any more influence on the binding of hum 250/183 than the TFβ-specific Mab BW 494/32 (Bosslet, et al., Cancer Immunol. Immunother. 23, 185–189, 1986). These data show that humanization of the Mab BW 250/183 has not measureably altered its epitope specificity, i.e. the specificity of the hum 250/183 is identical to that of the mouse Mab BW 250/183.

We claim:

1. An antibody light chain, containing a polypeptide of the amino acid sequence (SEQ ID No: 17)

Asp Ile Gln Met Thr Gln Ser Pro Ser Ser Leu Ser Ala Ser

Val Gly Asp Arg Val Thr Ile Thr Cys Arg Ala Ser Ser Ser

Val Ser Tyr Met His Trp Tyr Gln Gln Lys Pro Gly Lys Ala

Pro Lys Pro Leu Ile Tyr Ala Thr Ser Asn Leu Ala Ser Gly

Val Pro Ser Arg Phe Ser Gly Ser Gly Ser Gly Thr Asp Phe

Thr Phe Thr Ile Ser Ser Leu Gln Pro Glu Asp Ile Ala Thr

Tyr Tyr Cys Gln Gln Trp Ser Ser Asn Pro Leu Thr Phe Gly

Gln Gly Thr Lys Val Glu Ile Lys Arg.

2. A molecular construct containing at least one antibody as claimed in claim 1 and at least one further amino acid chain linked to the antibody chain, wherein said further amino acid chain is selected from the group consisting of: a heavy chain constant region, a light chain constant region, a part of a said heavy chain constant region, a part of said light chain constant region, and a peptide linker.

3. The molecular construct of claim 2, wherein the further amino acid chain is an antibody heavy chain constant region or part thereof.

4. The molecular construct as claimed in claim 3, wherein the molecular construct further contains an antibody heavy chain containing a polypeptide of the amino acid sequence Gln Val Gln Leu Gln Glu Ser Gly Pro Gly Leu Val Arg Pro Ser Gln Thr Leu Ser Leu Thr Cys Thr Val Ser Gly Phe Ser Asp Tyr Tyr Met Asn Trp Val Arg Gln Pro Pro Gly Arg Gly Leu Glu Trp Ile Gly Phe Ile Ser Asn Lys Pro Asn Gly His Thr Thr Glu Tyr Ser Ala Ser Val Lys Gly Arg Val Thr Met Leu Arg Asp Thr Ser Lys Asn Gln Phe Ser Leu Arg Leu Ser Ser Val Thr Ala Ala Asp Thr Ala Val Tyr Tyr Cys Ala Arg Asp Lys Gly Ile Arg Trp Tyr Phe Asp Val Trp Gly Gln Gly Ser Leu Val Thr Val Ser Ser 5. The molecular construct as claimed in claim 2, wherein the molecular construct is a single chain fragment.

6. The molecular construct as claimed in claim 2, wherein the molecular construct is a single domain fragment.

7. The molecular construct as claimed in claim 2, wherein the further amino acid chain is a part of a human antibody sequence and is not a sequence included in Table 1a or 1c.

8. The molecular construct of claim 7, wherein the molecular construct further contains an antibody heavy chain containing a polypeptide of the amino acid sequence (SEQ ID NO: 12)

Gln Val Gln Leu Gln Glu Ser Gly Pro Gly Leu Val Arg Pro Ser Gln

Thr Leu Ser Leu Thr Cys Thr Val Ser Gly Phe Ser Asp Tyr Tyr Met

Asn Trp Val Arg Gln Pro Pro Gly Arg Gly Leu Glu Trp Ile Gly Phe

Ile Ser Asn Lys Pro Asn Gly His Thr Thr Glu Tyr Ser Ala Ser Val

Lys Gly Arg Val Thr Met Leu Arg Asp Thr Ser Lys Asn Gln Phe Ser

Leu Arg Leu Ser Ser Val Thr Ala Ala Asp Thr Ala Val Tyr Try Cys

Ala Arg Asp Lys Gly Ile Arg Trp Tyr Phe Asp Val Trp Gly Gln Gly

Ser Leu Val Thr Val Thr Ser Ser or a Fab or F(ab') fragment thereof.

9. The molecular construct as claimed in claim 8 wherein the F(ab) or F(ab') fragment has a hinge region which is coded for by one or more hinge exons.

10. The molecular construct as claimed in claim 2, wherein the molecular construct is bound to an effector molecule.

11. Use of the molecular construct as claimed in claim 3 for detecting inflammations and/or for detecting tumors which are metastasizing into the bone marrow, preferably carcinoma of the breast, lymphoma, carcinoma of the prostate, or small-cell lung carcinoma.

12. A diagnostic agent containing a molecular construct as claimed in claim 3.

13. A medicament containing a molecular construct as claimed in claim 3.

* * * * *

UNITED STATES PATENT AND TRADEMARK OFFICE
CERTIFICATE OF CORRECTION

PATENT NO. : 5,645,817
DATED : July 08, 1997
INVENTOR(S) : Gerhard SEEMANN et al.

It is certified that error appears in the above-indentified patent and that said Letters Patent is hereby corrected as shown below:

Claim 4, column 23, line 61, "claim 3" should read --claim 2--.

Claim 11, column 25, line 30, "claim 3" should read --claim 2--.

Claim 12, column 26, line 27, "claim 3" should read --claim 2--.

Claim 13, column 26, line 29, "claim 3" should read --claim 2--.

Signed and Sealed this

Twentieth Day of January, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
      ( A ) LENGTH: 357 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:1:

```
CAGGTCCAAC  TGCAGGAGTC  TGGAGGAGGC  TTGGTACAGC  CTGGGGGTTC  TCTGAGACTC      60

TCCTGCGCAA  CTTCTGGGTT  CAGTGATTAC  TACATGAACT  GGGTCCGCCA  GCCTCCAGGA     120

AAAGCACTTG  AGTGGTTGGG  TTTTATTTCA  AACAAACCTA  ATGGTCACAC  AACAGAGTAC     180

AGTGCATCTG  TGAAGGGTCG  GTTCACCATC  TCCAGAGATA  ATTCCCAAAG  CATCCTCTAT     240

CTTCAAATGA  ACACCCTGAG  AGCTGAGGAC  AGTGCCACTT  ATTATTGTGC  AAGAGATAAG     300

GGAATACGAT  GGTACTTCGA  TGTCTGGGGC  CAAGGGACCA  CGGTCACCGT  CTCCTCA       357
```

( 2 ) INFORMATION FOR SEQ ID NO:2:

( i ) SEQUENCE CHARACTERISTICS:
      ( A ) LENGTH: 119 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:2:

```
Gln  Val  Gln  Leu  Gln  Glu  Ser  Gly  Gly  Gly  Leu  Val  Gln  Pro  Gly  Gly
 1              5                       10                      15

Ser  Leu  Arg  Leu  Ser  Cys  Ala  Thr  Ser  Gly  Phe  Ser  Asp  Tyr  Tyr  Met
             20                      25                      30

Asn  Trp  Val  Arg  Gln  Pro  Pro  Gly  Lys  Ala  Leu  Glu  Trp  Leu  Gly  Phe
             35                      40                      45

Ile  Ser  Asn  Lys  Pro  Asn  Gly  His  Thr  Thr  Glu  Tyr  Ser  Ala  Ser  Val
         50                      55                      60

Lys  Gly  Arg  Phe  Thr  Ile  Ser  Arg  Asp  Asn  Ser  Gln  Ser  Ile  Leu  Tyr
 65                      70                      75                      80

Leu  Gln  Met  Asn  Thr  Leu  Arg  Ala  Glu  Asp  Ser  Ala  Thr  Tyr  Tyr  Cys
```

```
                                   85                            90                              95
            Ala  Arg  Asp  Lys  Gly  Ile  Arg  Trp  Tyr  Phe  Asp  Val  Trp  Gly  Gln  Gly
                          100                      105                      110

Thr  Thr  Val  Thr  Val  Ser  Ser
                          115
```

( 2 ) INFORMATION FOR SEQ ID NO:3:

( i ) SEQUENCE CHARACTERISTICS:
        ( A ) LENGTH: 315 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GACATTCAGC  TGACCCAGTC  TCCAGCAATC  CTGTCTGCAT  CTCCAGGGGA  GAAGGTCACA      60
ATGACTTGCA  GGGCCAGCTC  AAGTGTAAGT  TACATGCACT  GGTACCAGCA  GAAGCCAGGA     120
TCCTCCCCCA  AACCCTGGAT  TTATGCCACA  TCCAACCTGG  CTTCTGGAGT  CCCTGCTCGC     180
TTCAGTGGCA  GTGGGTCTGG  GACCTCTTAC  TCTCTCACAA  TCATCAGAGT  GGAGGCTGAA     240
GATGCTGCCA  CTTATTACTG  CCAGCAGTGG  AGTAGTAACC  CGCTCACGTT  CGGTGCTGGG     300
ACCAAGCTGG  AGATC                                                         315
```

( 2 ) INFORMATION FOR SEQ ID NO:4:

( i ) SEQUENCE CHARACTERISTICS:
        ( A ) LENGTH: 105 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
            Asp  Ile  Gln  Leu  Thr  Gln  Ser  Pro  Ala  Ile  Leu  Ser  Ala  Ser  Pro  Gly
            1                    5                        10                       15

Glu  Lys  Val  Thr  Met  Thr  Cys  Arg  Ala  Ser  Ser  Ser  Val  Ser  Tyr  Met
                           20                       25                       30

His  Trp  Tyr  Gln  Gln  Lys  Pro  Gly  Ser  Ser  Pro  Lys  Pro  Trp  Ile  Tyr
                           35                       40                       45

Ala  Thr  Ser  Asn  Leu  Ala  Ser  Gly  Val  Pro  Ala  Arg  Phe  Ser  Gly  Ser
                      50                       55                       60

Gly  Ser  Gly  Thr  Ser  Tyr  Ser  Leu  Thr  Ile  Ile  Arg  Val  Trp  Ala  Glu
            65                        70                       75                       80

Asp  Ala  Ala  Thr  Tyr  Tyr  Cys  Gln  Gln  Trp  Ser  Ser  Asn  Pro  Leu  Thr
                                85                       90                       95

Phe  Gly  Ala  Gly  Thr  Lys  Leu  Glu  Ile
                           100                     105
```

( 2 ) INFORMATION FOR SEQ ID NO:5:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
CTGCTGGTAC  CAGTGCATGT  AACTTACACT  TGAGCTGGCC  CTACAGGTGA  TGGT            54
```

( 2 ) INFORMATION FOR SEQ ID NO:6:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
GCTTGGCACA CCAGAAGCCA GGTTGGATGT GGCGTAGATC AGCAG          45
```

( 2 ) INFORMATION FOR SEQ ID NO:7:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
CCCTTGGCCG AACGTGAGCG GGTTACTACT CCACTGCTGG CAGTAGTAGG T    51
```

( 2 ) INFORMATION FOR SEQ ID NO:8:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
CTGTCTCACC CAGTTCATGT AGTAATCGCT GAAGCCAGAC ACGTT          45
```

( 2 ) INFORMATION FOR SEQ ID NO:9:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
CTTGCTGGTG TCTCTGAGCA TTGTCACTCT ACCCTTCACG GATGCGCTGT ACTCGGTTGT    60
GTGTCCGTTA GGCTTGTTTG AAATAAATCC AATCCACTC                          99
```

( 2 ) INFORMATION FOR SEQ ID NO:10:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
GCCTGGACCC CAGACATCGA AGTACCATCG TATTCCCTTA TCTCTTGCAC AATA    54
```

( 2 ) INFORMATION FOR SEQ ID NO:11:

( i ) SEQUENCE CHARACTERISTICS:
  ( A ) LENGTH: 357 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:11:

| | | | | | |
|---|---|---|---|---|---|
| CAGGTCCAAC | TGCAGGAGAG | CGGTCCAGGT | CTTGTGAGAC | CTAGCCAGAC | CCTGAGCCTG | 60 |
| ACCTGCACCG | TGTCTGGCTT | CAGCGATTAC | TACATGAACT | GGGTGAGACA | GCCACCTGGA | 120 |
| CGAGGTCTTG | AGTGGATTGG | ATTTATTTCA | AACAAACCTA | ATGGTCACAC | AACAGAGTAC | 180 |
| AGTGCATCTG | TGAAGGGTAG | AGTGACAATG | CTGCGAGACA | CCAGCAAGAA | CCAGTTCAGC | 240 |
| CTGAGACTCA | GCAGCGTGAC | AGCCGCCGAC | ACCGCGGTCT | ATTATTGTGC | AAGAGATAAG | 300 |
| GGAATACGAT | GGTACTTCGA | TGTCTGGGGT | CAAGGCAGCC | TCGTCACAGT | CTCCTCA | 357 |

( 2 ) INFORMATION FOR SEQ ID NO:12:

( i ) SEQUENCE CHARACTERISTICS:
  ( A ) LENGTH: 119 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:12:

```
Gln Val Gln Leu Gln Glu Ser Gly Pro Gly Leu Val Arg Pro Ser Gln
  1               5                  10                  15

Thr Leu Ser Leu Thr Cys Thr Val Ser Gly Phe Ser Asp Tyr Tyr Met
             20                  25                  30

Asn Trp Val Arg Gln Pro Pro Gly Arg Gly Leu Glu Trp Ile Gly Phe
         35                  40                  45

Ile Ser Asn Lys Pro Asn Gly His Thr Thr Glu Tyr Ser Ala Ser Val
     50                  55                  60

Lys Gly Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Asp Lys Gly Ile Arg Trp Tyr Phe Asp Val Trp Gly Gln Gly
             100                 105                 110

Ser Leu Val Thr Val Ser Ser
             115
```

( 2 ) INFORMATION FOR SEQ ID NO:13:

( i ) SEQUENCE CHARACTERISTICS:
  ( A ) LENGTH: 321 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:13:

| | | | | | |
|---|---|---|---|---|---|
| GACATCCAGA | TGACCCAGAG | CCCAAGCAGC | CTGAGCGCCA | GCGTGGGTGA | CAGAGTGACC | 60 |
| ATCACCTGTA | GGGCCAGCTC | AAGTGTAAGT | TACATGCACT | GGTACCAGCA | GAAGCCAGGT | 120 |
| AAGGCTCCAA | AGCTGCTGAT | CTACGCCACA | TCCAACCTGG | CTTCTGGTGT | GCCAAGCAGA | 180 |
| TTCAGCGGTA | GCGGTAGCGG | TACCGACTTC | ACCTTCACCA | TCAGCAGCCT | CCAGCCAGAG | 240 |

```
GACATCGCCA CCTACTACTG CCAGCAGTGG AGTAGTAACC CGCTCACGTT CGGCCAAGGG        300

ACCAAGGTGG AAATCAAACG T                                                  321
```

( 2 ) INFORMATION FOR SEQ ID NO:14:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Ser Val Ser Tyr Met
             20                  25                  30

His Trp Tyr Gln Gln Lys Pro Gly Lys Ala Pro Lys Leu Leu Ile Tyr
         35                  40                  45

Ala Thr Ser Asn Leu Ala Ser Gly Val Pro Ser Arg Phe Ser Gly Ser
     50                  55                  60

Gly Ser Gly Thr Asp Phe Thr Phe Thr Ile Ser Ser Leu Gln Pro Glu
 65              70                  75                  80

Asp Ile Ala Thr Tyr Tyr Cys Gln Gln Trp Ser Ser Asn Pro Leu Thr
             85                  90                  95

Phe Gly Gln Gly Thr Lys Val Glu Ile Lys Arg
            100                 105
```

( 2 ) INFORMATION FOR SEQ ID NO:15:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
GCTTGGCACA CCAGAAGCCA GGTTGGATGT GGCGTAGATC AGCGGCTTTG GAGCCTT           57
```

( 2 ) INFORMATION FOR SEQ ID NO:16:

( i ) SEQUENCE CHARACTERISTICS:
        ( A ) LENGTH: 321 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
GACATCCAGA TGACCCAGAG CCCAAGCAGC CTGAGCGCCA GCGTGGGTGA CAGAGTGACC        60

ATCACCTGTA GGGCCAGCTC AAGTGTAAGT TACATGCACT GGTACCAGCA GAAGCCAGGT       120

AAGGCTCCAA AGCCGCTGAT CTACGCCACA TCCAACCTGG CTTCTGGTGT GCCAAGCAGA       180

TTCAGCGGTA GCGGTAGCGG TACCGACTTC ACCTTCACCA TCAGCAGCCT CCAGCCAGAG       240

GACATCGCCA CCTACTACTG CCAGCAGTGG AGTAGTAACC CGCTCACGTT CGGCCAAGGG       300

ACCAAGGTGG AAATCAAACG T                                                 321
```

( 2 ) INFORMATION FOR SEQ ID NO:17:

(i) SEQUENCE CHARACTERISTICS:
 (A) LENGTH: 107 amino acids
 (B) TYPE: amino acid
 (D) TOPOLOGY: linear (ii) MOLECULE TYPE: peptide (xi) SEQUENCE DESCRIPTION: SEQ ID NO:17:

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Ser Ser Val Ser Tyr Met
            20                  25                  30
His Trp Tyr Gln Gln Lys Pro Gly Lys Ala Pro Lys Pro Leu Ile Tyr
        35                  40              45
Ala Thr Ser Asn Leu Ala Ser Gly Val Pro Ser Arg Phe Ser Gly Ser
    50                  55                  60
Gly Ser Gly Thr Asp Phe Thr Phe Thr Ile Ser Ser Leu Gln Pro Glu
65              70                      75                  80
Asp Ile Ala Thr Tyr Tyr Cys Gln Gln Trp Ser Ser Asn Pro Leu Thr
                85                  90                  95
Phe Gly Gln Gly Thr Lys Val Glu Ile Lys Arg
                100                 105
```